United States Patent [19]

Kocal

[11] Patent Number: 5,034,564
[45] Date of Patent: Jul. 23, 1991

[54] PRODUCTION OF ALKYL AROMATIC COMPOUNDS

[75] Inventor: Joseph A. Kocal, Gurnee, Ill.

[73] Assignee: UOP, Des Plaines, Ill.

[21] Appl. No.: 507,812

[22] Filed: Apr. 12, 1990

[51] Int. Cl.$^5$ .............................................. C07C 2/68
[52] U.S. Cl. .................................................... 585/467
[58] Field of Search ....................................... 585/467

[56] References Cited

U.S. PATENT DOCUMENTS

| | | | |
|---|---|---|---|
| 3,965,043 | 6/1976 | Stridde | 252/455 R |
| 3,979,331 | 9/1976 | Stridde | 252/441 |
| 4,499,195 | 2/1985 | Wheelock | 502/63 |
| 4,499,319 | 2/1985 | Ballantine et al. | 585/467 |
| 4,587,009 | 5/1986 | Wheelock | 208/111 |
| 4,605,806 | 8/1986 | Ballantine et al. | 585/467 |
| 4,719,191 | 1/1988 | Battiste et al. | 502/84 |

OTHER PUBLICATIONS

Adams, J. M., "Synthetic Organic Chemistry Using Pillared Cation-Exchanged and Acid-Treated Montmorillonite Catalysts—A Review," *Applied Clay Science*, 2, pp. 309-342 (1987).

*Primary Examiner*—Curtis R. Davis
*Attorney, Agent, or Firm*—Thomas K. McBride; Raymond H. Nelson

[57] ABSTRACT

Alkyl aromatic compounds may be prepared by reacting an aromatic compound such as benzene with an alkylating agent such as an olefin, alkyl halide or alkyl alcohol in the presence of an alkylation catalyst. The alkylation catalyst of the present invention comprises a pillared clay and a binder which has been prepared by dispersing a clay in a metallic pillaring agent sol, separating the resultant pillared clay, washing and drying said pillared clay, forming a dough of said pillared clay and a binder compound, extruding said dough extudate. By utilizing this catalytic composite it is possible to obtain improved selectivity of the desired alkyl aromatic compound which may then be used in the preparation of biodegradable detergents.

14 Claims, No Drawings

PRODUCTION OF ALKYL AROMATIC COMPOUNDS

Alkyl aromatic compounds form important chemicals which may be utilized as intermediates in many industrial applications as, for example, polymeric material, plasticizers, detergents, etc. Heretofore, the production of alkyl aromatic compounds has been effected by alkylating an aromatic compound with an alkylating agent in the presence of acidic catalysts. These acidic catalysts include sulfuric acid and hydrofluoric acid due to the relatively good activity for the purpose intended. However, the use of these liquid acids such as sulfuric acid or hydrofluoric acid has inherently some drawbacks or shortcomings. The acids hereinbefore named are extremely corrosive in nature, thus requiring special handling and equipment due to the dangerous nature thereof. In addition, the use of these acids might also involve some environmentally hazardous problems which are attendant thereto. Therefore, it would be preferable to utilize a safer and more simple catalyst, preferentially in solid state, in a fixed bed reactor to produce the desired compounds. The use of a simpler process would result in less capital investment and therefore enable the producer to provide a less expensive product.

In view of this we have now discovered that a solid alkylation catalyst may be employed to effect the desired alkylation to obtain a production which is equal in quality to those products obtained when utilizing liquid acidic catalyst while also improving the activity of the catalyst as well, as the selectivity of the product.

Naturally occurring clays such as smectites, vermiculites and bentonites are composed of semicrystalline aluminosilicate layers (lamellae) held together by Van der Waals and electrostatic forces. Anionic charges on the siliceous layers are neutralized by cations in the interlamellar spaces. These cations, usually $Na^+$, $Ca^{+2}$, can be ion exchanged with large inorganic cations such as $Fe^{+3}$, $Cr^{+3}$ or with metal hydroxy polymer cations such as $[Al_{13}O_4(OH)_{24}(H_2O)_{12}]^{+7}$ or $[Zr(OH)_2\cdot 4H_2O]_4^{8+}$. The polymeric cations act as pillars, propping the clay layers apart.

Pillared clays are known to catalyze numerous reactions such as alkylation, cracking, ester formation, dimerization, oligomerization, etc. A review of the reactions catalyzed by pillared clays may be found in an 0 article by J.M. Adams, *Applied Clay Science*, 2, pp. 309–342 (1987). Of these reactions, alkylation has received considerable attention. For example, U.S. Pat. No. 4,499,319 discloses layered clays such as montmorillonite which have been ion-exchanged with metal cations such as chromium and aluminum, which are used to alkylate aromatic compounds. Other examples include U.S. Pat. No. 4,605,806 which discloses a hydrogen ion-exchanged pillared clay; U.S. Pat. No. 3,965,043 discloses a metallic cation exchanged trioctahedral 2:1 layer-lattice smectite-type clay and U.S. Pat. No. 3,979,331 which discloses a metallic cation exchanged synthetic hectorite-type clay useful for alkylating aromatic hydrocarbons.

Another reference is U.S. Pat. No. 4,499,195 which discloses a co-gel of a smectite clay with an inorganic metal oxide to produce a co-gel. The inorganic oxides include Group IV-B metal oxides and other oxides such as silicon, aluminum, thorium and uranium. However, since the metal oxide gel is stated to be formed before addition of the clay, it appears that the clay is not homogeneously dispersed in the metal oxide gel. A continuation-in-part of the '195 reference (U.S. Pat. No. 4,587,009) discloses the use of the co-gel for hydrogenation of hydrocarbons.

Another U.S. Pat., namely No. 4,719,191, discloses a pillared clay which has been reacted with a stabilizing agent.

In contrast to these patents, it has now been discovered that the alkylation of aromatic compounds may be accomplished by utilizing a pillared clay which has been admixed with a binder compound and the resulting dough extruded, dried and calcined to form the desired catalytic composition of matter. The resulting catalyst will possess excellent characteristics with respect to the activity of the catalyst as well as to the selectivity of the product which is obtained by the alkylation reaction.

BRIEF SUMMARY OF THE INVENTION

This invention relates to a process for producing alkyl aromatic compounds as well as to a catalyst which may be used to effect the desired reaction. As was previously set forth, alkyl aromatic compounds may be utilized in many and varied industrial applications. For example, one of the major problems which is prevalent in population centers throughout the world is the disposal of sewage containing detergents dissolved therein. Such disposal problems are especially trying in instances where the detergents comprised branched chain alkyl aryl compounds. These branched chain detergents produce stable foams in either hard or soft waters in such large quantities that the foam tends to clog sewage treatment facilities and destroy the bacteria which are necessary for proper sewage treatment. These unwanted foams or suds are found in many rivers, streams, lakes, etc. which provide a water supply for the aforesaid population centers. As hereinbefore set forth, the presence of these unwanted foams or suds is due in many instances to the use of detergents which are non-biodegradable in nature and which will not break down due to bacterial action thereon. This non-biodegradable nature of the detergents is due to the fact that the alkyl side chain of the molecule is, in many instances, highly branched in nature and therefore is not readily attacked by organisms which would ordinarily destroy the molecules. In contradistinction to this, the presence of straight chain alkyl substituents on the ring will permit bacteria to act upon the alkyl chain and destroy the detergents, thereby minimizing the formation of foams or suds which will then not build up on the surface of the water.

By utilizing the catalytic composition of matter of the present invention, it is possible to obtain straight chain alkyl aryl detergents due to the excellent selectivity characteristics of the catalyst, especially with regard to alpha-olefins to obtain the desired alkyl aromatic product. As will hereinafter be shown in greater detail when utilizing the particular catalytic composition of matter of the present invention, it is possible to effect an alkylation process in which the activity of the catalyst will be maintained for a relatively lengthy period of time as well as obtaining a selective product from the reaction.

It is therefore an object of this invention to provide a catalytic composition of matter which may be used to effect an alkylation of aromatic compounds.

A further object of this invention is to provide a process for preparing such catalytic composition of matter and in addition to provide the necessary process for producing an alkyl aromatic compound.

In one aspect an embodiment of this invention resides in a process for the production of an alkylaromatic compound which comprises reacting an aromatic compound with an alkylating agent selected from the group consisting of olefins, alkyl halides and alkyl alcohols at alkylating conditions in an alkylation zone in the presence of a catalytic composition of matter, said catalytic composition of matter having been prepared by dispersing a clay in a metallic pillaring agent sol, separating the resultant pillared clay, washing and drying said pillared clay, forming a dough of said pillared clay and a binder compound, extruding said dough and calcining the resulting extrudate, and recovering said alkyl aromatic compound.

A specific embodiment of this invention is found in a process for production of an aromatic compound which comprises reacting benzene with an alkylating agent comprising a mixture of olefins containing from 9 to about 15 carbon atoms in the chain at a temperature in the range of from about 80° to about 450° C. and a pressure in the range of from about 200 to about 1000 pounds per square inch gauge in the presence of a catalyst, said catalyst having been prepared by dispersing a clay comprising bentonite in a metallic pillaring agent sol comprising a solution of aluminum chlorohydrol, separating the pillared clay, washing said pillared clay and drying the clay, thereafter forming a dough by admixing said dried clay with a solution of alumina, extruding the dough, drying said dough, and calcining the dried extrudate to form the desired catalyst, and recovering said alkylated benzene.

Other objects and embodiments will be found in the following further detailed description of the invention.

DETAILED DESCRIPTION OF THE INVENTION

As was hereinbefore set forth, the present invention is concerned with a catalyst which is useful in the alkylation of aromatic compounds and particularly to a catalytic composite which will possess excellent characteristics with respect to activity and selectivity of the alkyl aromatic compound which is produced during the reaction.

The catalytic composite of the present invention comprises a pillared clay which has been treated with a binder compound and extruded, following which the extrudate is dried and calcined to form the desired catalyst.

One component of the catalyst of the present invention comprises a clay. Both natural and synthetic clays may be used including but not limited to bentonite, sepiolite, laponite TM, vermiculite, montmorillonite, kaolin, palygorskite (attapulgus), hectorite, chlorite, beidellite, saponite and nontronite. Of the above clays laponite TM is a synthetic clay (manufacture by La-Porte Co.) and montmorillonite, hectorite, beidellite and saponite have synthetic analogs. The clays (both natural and synthetic analogs) may be used as they occur (or as synthesized) or they may be modified by exchanging with metals or introducing pillars between the layers to give pillared clays. Any of the clays, including all the ones enumerated above, may be exchanged with one or more metals selected from the group consisting of $Fe^{+3}$, $Cr^{+3}$, $Al^{+3}$, $Ti^{+4}$, and $Zr^{+4}$. The clays into which pillars may be introduced are the smectite clays (natural and synthetic) which are hectorite, beidellite, laponite TM, nontronite, saponite and montmorillonite.

The above-mentioned clays may be pillared by any means known utilizing, as a metallic pillaring agent, in particular, the oxychlorides of aluminum, zirconium, lanthanum, cerium and titanium. It is to be understood that the aforementioned list of clays, both natural and synthetic in nature, as well as metallic pillaring agents are only representative of the types of clays and agents which may be used in the present invention, and that the present invention is not necessarily limited thereto. After pillaring the clay by dispersing the clay in a solution of the pillaring agent, the resultant pillared clay is separated from the mother liquor, water washed to remove any excess metallic salt and dried.

The dried pillared clay is then admixed with a binder compound which in the preferred embodiment of the invention comprises silica, alumina, titania, zirconia, aluminum phosphate, etc. Again, it is to be understood that these compounds are only representative of the type of binder compounds which may be used and that the present invention is not necessarily limited thereto. The admixing of the pillared and binder compound is accomplished by adding the pillared clay to a paste of the binder compound to form a dough. The dough is then extruded through a die to obtain the desired particle shape and size of the catalyst following which it is then dried at a temperature of from about ambient (20°–25° C. up to about 150° C.) for a period of time dependent upon the temperature which is employed and which may range from about one hour to about sixteen hours. Following the drying of the extrudate, it is then calcined in an air atmosphere or an air atmosphere which contains from one to about twenty percent steam at a temperature in the range of from about 300° up to about 800° C. for a period of time which may range from about one to about twenty-four hours.

The alkylation of aromatic compounds utilizing the catalytic composite of the present invention may be effected in any suitable manner utilizing either a batch type or a continuous type operation. The aromatic compounds which are treated with an alkylating agent may comprise either monocyclic or polycyclic compounds. In addition, the aromatic compounds may also contain substituents on the ring, examples of the aromatic compounds including benzene, toluene, o-xylene, m-xylene, p-xylene, ethylbenzene, naphthalene, isomeric methyl naphthalenes, isomeric ethyl naphthalenes, anthracene, chrysene, pyrene, etc. Alkylating agents which are utilized as the second component in the process will comprise olefins containing from 2 to about 20 carbon atoms, alkyl halides, alcohols, etc. Some specific examples of these alkylating agents will include ethylene, propylene, the isomeric butenes, pentenes, hexenes, heptenes, octenes, nonenes, decenes, undecenes, dodecenes, tridecenes, tetradecenes, pentadecenes, hexadecenes, heptadecenes, octadecenes, nonadecenes, eicosenes, etc., methyl chloride, ethyl chloride, propyl chloride, butyl chloride, hexyl chloride, octyl chloride, decyl chloride, dodecyl chloride, tetradecyl chloride, methyl bromide, ethyl bromide, propyl bromide, butyl bromide, heptyl bromide, nonyl bromide, undecyl bromide, etc., methyl alcohol, ethyl alcohol, propyl alcohol, isopropryl alcohol, n-butyl alcohol, sec-butyl alcohol, etc. In addition, it is also contemplated that mixtures of olefins may also be employed as alkylating agents. It is to be understood that the aforementioned aromatic compounds and alkylating agents are only representative of the type of compounds which may be employed as reactants in the alkylation process and that the present invention is not necessarily limited to these compounds.

The alkylation reaction may be effected in a batch type operation by placing the aromatic compound and the alkylating agent in an appropriate apparatus such as an autoclave of the rotating or mixing type along with the catalytic composite. In the preferred embodiment of the invention the alkyl aromatic compound is present in the reaction mixture in an excess of alkylating agent, preferably in a range of from about 2:1 to about 20:1 moles of aromatic, compound per mole of alkylating agent. The reactor is sealed and heated to the desired operating temperature which may be in a range of from about 80° to about 450° C. In addition, in order to preferably effect the reaction in a liquid phase pressure is added to maintain an operating pressure in the range of from about 200 to about 1,000 pounds per square inch gauge. The operating pressure which is employed may be provided for by the introduction of an inert gas such as nitrogen, helium, argon, etc. when the alkylating agent is in liquid form. Conversely, if the alkylating agent which is employed is in gaseous form a portion of the operating pressure may be afforded by the autogenous pressure of the gaseous alkylating agent while the remainder is afforded by the presence of an inert gas. Upon completion of the reaction time which may range from about 0.5 up to about 4 hours or more in duration, heating is discontinued and after the reactor and contents thereof have returned to room temperature excess pressure is vented, the autoclave is opened and the reaction mixture is recovered therefrom. The desired alkyl aromatic compound may then be separated from any unreacted starting materials by conventional means such as fractional distillation and recovered.

When the alkylation reaction of the present invention is effected in a continuous manner a quantity of the catalytic composite is placed in a reactor which may be tubular in configuration. The reactor is heated to the desired operating temperature and brought up to the desired operating pressure, following which the reactants comprising the aromatic compound and the alkylating agent are continuously passed over the catalyst bed at a predetermined liquid hourly space velocity. After passage through the catalyst bed for a predetermined period of time the reactor effluent is continuously withdrawn and subjected to conventional separation means whereby the desired alkyl aromatic, product is separated and recovered while any unreacted starting materials may be recycled to the reactor to form a portion of the feedstock.

Inasmuch as the catalytic composite of the present invention is solid in nature, various types of continuous operation may be employed. For example, the catalyst may be maintained in the reactor as a fixed bed while the aromatic compound and alkylating agent are passed through the bed in either an upward or downward flow. Alternatively, a moving bed type of operation may be employed in which the catalyst bed and the reactants are passed through the reactor either concurrently or countercurrently to each other. Likewise, a slurry type operation may be employed in which the catalyst is carried into the reactor as a slurry in one or both of the reactants.

As will hereinafter be shown in the following examples, which are given for purposes of illustrating the catalyst and the process of the present invention, the catalysts of said invention will provide a product selectivity superior to that which is obtained when utilizing catalyst heretofore known in the prior art. However, it is to be understood that these examples are given merely for purposes of illustration, and that the present invention is not necessarily limited thereto.

EXAMPLE I

A pillaring agent was prepared by diluting a 50 percent solution of aluminum chlorohydrol with sufficient water to form a 0.484 mol solution. The solution was then digested for a period three hours at a temperature of 95 degrees C. to form the desired pillaring agent. Following this a bentonite clay was dispersed in the pillaring agent for a period of two hours at a temperature of about 65 degrees C. The amount of clay utilized was that which was sufficient to satisfy an aluminum/clay ratio of 7.0 millimol of aluminum, per gram of anhydrous clay. The clay, after being pillared with the aluminum compound, was separated from the mother liquor and thereafter thoroughly washed with water to remove any excess aluminum sol and to reduce the chlorine level in the pillared clay. Thereafter the pillared clay cake was dried at a temperature of about 100 degrees C. in thin sheets to avoid particulate agglomeration.

The desired catalyst was then prepared by wetting 200 grams of alumina with 800 grams of deionized water and admixed in a thorough manner. Thereafter 29.1 cc of nitric acid was slowly added with thorough admixing. Thereafter 800 grams of the pillared clay which had been prepared according to the above paragraph was added to the alumina mixture with thorough admixing of the compounds. The resulting dough was extruded through a die to form 1/32 inch diameter extrudate. These extrudates were then dried at a temperature ranging between 110 degrees and 150 degrees C. for a period of about 16 hours following which the extrudates were calcined in a flowing air atmosphere by placing the extrudates in an oven, raising the temperature to 400 degrees C. during a period of two hours and holding at this 400 degree C. temperature for an additional period of two hours. Following this the extrudates were recovered and designated as catalyst A. For comparison purposes, the extrudates were washed and sized over a 10 to 40 mesh range for testing.

EXAMPLE II

A second catalyst was prepared by pillaring a bentonite clay in a manner similar to that set forth in the Example I above, that is, a solution of aluminum chlorohydrol was diluted with water and allowed to digest for a period of three hours at a temperature of 95 degrees C. to form the pillaring agent. Following this the bentonite clay was dispersed in the pillaring agent, said dispersion being maintained for a period of two hours at a temperature of about 65 degrees C. The clay, after being pillared with the aluminum solution, was separated from the mother liquor, dried to form a filter cake and calcined at a temperature of 400 degrees C. for a period of two hours. The pillared clay was then sized to 10–40 mesh for testing purposes. This catalyst was designated as Catalyst B.

EXAMPLE III

A third catalyst which was used for comparison purposes comprised a clay known in the trade as Filtrol 24 which is a montmorillonite type of clay. This catalyst was designated as Catalyst C.

EXAMPLE IV

The three catalysts of Examples I through III were utilized in an alkylation reaction by placing 25 cc of each catalyst in tubular stainless steel reactors having an inside diameter of ½ inch. A feedstock comprising a mixture of benzene and an alkylating agent consisting of a mixture of olefins containing from ten to fourteen carbon atoms in a benzene/olefin feed molar ratio of 8:1 was charged to the reactor at a liquid hourly space velocity of 2 hours$^{-1}$. The reactor was maintained at a temperature of 150 degrees C under a pressure of 500 pounds per square inch gauge. The product which was recovered from the reactor was analyzed to determine the percent of olefin conversion, the percent of detergent alkylate selectivity and the percent of linearity. The results of these analyses are set forth in the Table below.

TABLE

| Catalyst | A | B | C |
|---|---|---|---|
| Olefin Conversion % | 100 | 100 | 100 |
| Detergent Alkylate Selectivity wt. % | 88 | 84 | 79 |
| Linearity % | 93 | 92 | 92 |

It will be noted from the above table that the detergent alkylate selectivity which may be defined as the weight of total monoalkyl benzenes divided by the total weight of all products including dialkyl benzenes, olefinic oligomers and monoalkyl benzenes is greater in all instances where the catalyst of the present invention comprises a pillared clay admixed with a binder as compared to the catalysts which do not contain the binder. This, therefore, clearly indicates that the presence of the binder in conjunction with the pillared clay results in the obtainment of a greater amount of desired product comprising monoalkyl benzene which may then be used as an intermediate in the preparation of biodegradable detergents.

I claim as my invention:

1. A process for the production of an alkylaromatic compound which comprises reacting an aromatic compound with an alkylating agent selected from the group consisting of olefins, alkyl halides and alkyl alcohols at alkylating conditions in an alkylation zone in the presence of a catalytic composition of matter, said catalytic composition of matter having been prepared by dispersing a clay in a metallic pillaring agent sol, separating the resultant pillared clay, washing and drying said pillared clay, forming a dough of said pillared clay and a binder compound, extruding said dough and calcining the resulting extrudate, and recovering said alkyl aromatic compound.

2. The process as set forth in claim 1 in which said alkylation conditions include a temperature in the range of from about 80° to about 450° C. and a pressure in the range of from about 200 to about 1,000 pounds per square inch gauge.

3. The process as set forth in claim 1 in which said alkylating agent contains from about 1 to about 20 carbon atoms.

4. The process as set forth in claim 3 in which said alkylating agent contains from about 9 to about 15 carbon atoms.

5. The process as set forth in claim 1 in which said aromatic compound and said alkylating agent are present in said alkylation zone in a mole ratio of aromatic compound to alkylating agent in a range of from about 2:1 to about 20:1.

6. The process as set forth in claim 1 in which said aromatic compound comprises benzene.

7. The process as set forth in claim 1 in which said aromatic compound comprises toluene.

8. The process as set forth in claim 1 in which said aromatic compound comprises naphthalene.

9. The process as set forth in claim 1 in which said clay is selected from the group consisting of bentonite, vermiculite, montmorillonite, kaolin, sepiolite, polygorskite, hectorite, chlorite, beidellite, saponite, nontronite and mixtures thereof.

10. The process as set forth in claim 1 in which said metallic pillaring agent is selected from the group consisting of oxychlorides of aluminum, zirconium, lanthanum, cerium and titanium.

11. The process as set forth in claim 1 in which said binder compound is selected from the group consisting of alumina, silica, titania, zirconia and aluminum phosphate.

12. The process as set forth in claim 11 in which said binder compound is present in an amount in the range of from about 5% to about 50% by weight of said pillared clay.

13. The process as set forth in claim 1 in which the calcination of said dough of a pillared clay and a binder compound is effected at a temperature in the range of from about 300° to about 800° C.

14. The process as set forth in claim 11 wherein said binder is alumina.

* * * * *